US005612021A

United States Patent [19]

Mellul

[11] Patent Number: 5,612,021

[45] Date of Patent: Mar. 18, 1997

[54] COSMETIC MAKE-UP COMPOSITION CONTAINING A FULLERENE OR MIXTURE OF FULLERENES AS A PIGMENTING AGENT

[75] Inventor: Myriam Mellul, L'Hay les Roses, France

[73] Assignee: L'Oreal, Paris, France

[21] Appl. No.: 453,728

[22] Filed: May 30, 1995

Related U.S. Application Data

[63] Continuation of Ser. No. 150,732, Nov. 12, 1993, abandoned.

[30] Foreign Application Priority Data

Nov. 13, 1992 [FR] France .................................. 92 13675

[51] Int. Cl.[6] .............................. A61K 7/043; A61K 7/48

[52] U.S. Cl. .............................. 424/61; 424/401; 424/65; 424/64; 424/707; 424/DIG. 5; 514/844; 514/845; 514/846; 514/937; 514/938; 514/943; 514/944

[58] Field of Search ................................ 424/401, 61, 63, 424/64, 707, DIG. 5; 514/844, 845, 896, 937, 938, 943, 944

[56] References Cited

U.S. PATENT DOCUMENTS

| | | | |
|---|---|---|---|
| 5,114,477 | 5/1992 | Mort et al. | 106/20 |
| 5,188,918 | 2/1993 | Ziolo | 430/106 |

OTHER PUBLICATIONS

JP (93) 5017328, Abstract.

Harry's Cosmeticology By Ralph Harry, pp. 123–144, 155–174 (1973).

Database WPIL, Week 9309, Derwent Publications Ltd., London, GB; An 93–71008 & JP-A-517 328 (Kanebo).

Database WPIL, Week 9309, Derwent Publications Ltd., London, GB; An 93–71007 & JP-A-517 327 (Kanebo).

*Primary Examiner*—Jyothsna Venkat
*Attorney, Agent, or Firm*—Oliff & Berridge

[57] ABSTRACT

Cosmetic make-up composition containing, in a suitable vehicle, as a filler and/or pigment, a fullerene or mixture of fullerenes; use of such a composition.

25 Claims, No Drawings

COSMETIC MAKE-UP COMPOSITION CONTAINING A FULLERENE OR MIXTURE OF FULLERENES AS A PIGMENTING AGENT

This is a continuation of application Ser. No. 08/150,732 filed Nov. 12, 1993, now abandoned.

The present invention relates to a cosmetic composition for making up, in particular, the skin, eyes, nails and hair, containing as fillers or pigments a fullerene or a mixture of fullerenes.

Face make-up products are essentially eyeshadows, eyeliners, mascaras, powders, make-up foundations, rouges, blushers, tinted creams, conventional and slim style lipsticks or else concealer sticks.

All these products, as well as, moreover, nail varnishes, contain variable proportions of pigments and/or inorganic fillers designed to endow these products with a certain colour, as well as, moreover, various cosmetic properties such as good covering power and pleasant application characteristics.

Among the pigments and inorganic fillers commonly used in cosmetics, there may be mentioned:

- ground natural inorganic compounds such as talc, sericite, mica, and the like,
- metal oxides obtained synthetically or of natural origin, such as iron, titanium, zinc and chromium oxide, and the like,
- synthetic inorganic compounds such as boron nitride, bismuth oxychloride, titanium dioxide-coated mica, and the like,
- pure metals such as, for example, aluminium flakes, and
- some special compounds such as manganese pyrophosphate, ultramarine blue and Prussian blue, the latter compounds being used only for their colouring power.

Carbon black and synthetic or natural melanin are also used as a source of pigment.

Among all these compounds, formulators have at their disposal only a small number of dark brown to black pigments, these essentially being black iron oxide, carbon black and melanin. Other pigments are sometimes used, but their black pigmentary power is low, for example graphite.

Carbon black is widely used in eyeliners, but is difficult to disperse on account of its small particle size. The agglomerates formed compel the use of effective grinding and dispersion systems, and this is often reflected in rises in viscosity of the media.

Black iron oxide does not present problems of dispersion, but its dyeing power is only average and it is unstable at high temperature.

It has now been found that fullerenes, a third organized variety of carbon, the other two being diamond and graphite, could constitute excellent pigments in cosmetic make-up compositions.

The molecular fullerenes, as is now well known, consist of completely closed hollow spheres of carbon atoms containing from 32 to 1,000 or more carbon atoms in each sphere.

For a more detailed description, reference may be made to the following articles: R. E. SMALLEY, "Supersonic Carbon Cluster Beams in Atomic and Molecular Clusters"; E. R. BERSTEIN Ed., Physical and Theoretical Chemistry, Vol. 68, Elsevier Science, New York, 1990, pp. 1–68; R. F. CURL et al., "Fullerenes", Scientific American, pp. 32–41, October 1991; F. DIEDERICH et al., "The Higher Fullerenes: Isolation and Characterization", Science, Vol. 252, pp.

548–551, April 1991; and R. E. SMALLEY "Great Balls of Carbon: The Story of Buckminsterfullerene", The Sciences, Vol. 31, No. 2, pp. 22–28, March–April 1991.

Among fullerenes, the most typical is $C_{60}$, the structure of which recalls that of a football. Other fullerenes exist, especially $C_{70}$ as well as $C_{84}$. The fullerenes are now commonly known as "buckyballs".

The molecules of $C_{60}$ fullerenes are, moreover, generally contaminated with small amounts of $C_{70}$ and $C_{84}$ molecules.

The preparation of fullerenes together with their solubility, crystallinity and colour characteristics have been described in many publications, and in particular by W. KRÄTSCHMER et al., Nature, Vol. 347, pp. 354–358, 1990 and in Chemical and Engineering News, pp. 22–25, October 1990.

The subject of the present invention is hence cosmetic make-up composition containing, in a suitable cosmetic vehicle, as a filler and/or pigment, a fullerene or mixture of fullerenes.

The fullerenes of the compositions according to the invention are $C_{60}$, $C_{70}$ and $C_{84}$, and mixtures thereof.

Preferably, the fullerene is $C_{60}$ containing a small proportion of $C_{70}$ as well as, where appropriate, of $C_{84}$.

The coloration of the fullerenes is dependent on the arrangement of the carbon atoms, and can extend from yellow-orange to black.

Independently of their use as pigments in the cosmetic compositions, the fullerenes confer, moreover, good cosmetic properties, in particular a good ease of spreading and a great softness to the touch.

Among the fullerenes which may be used in the compositions according to the invention, there may be mentioned especially those supplied by company TEXAS FULLERENES CORPORATION, Houston, Tex., the company MATERIAL AND ELECTROCHEMICAL RESEARCH CORPORATION, Tucson, Ariz., the company RESEARCH MATERIALS INC., Golden, Colo. and the company ALDRICH, the latter marketing a $C_{60}/C_{70}$ fullerene under the name "Fullerite".

The cosmetic compositions in which the fullerenes may be employed are essentially those relating to face make-up, that is to say eyeshadows, eyeliners, mascaras, powders, make-up foundations, rouges, blushers, tinted creams, conventional and slim style lipsticks or concealer sticks, but also to hair make-up.

Fullerenes also find application in nail varnishes in an aqueous medium.

Preferably, the cosmetic compositions according to the invention are more especially intended for making up the eyes, that is to say are in the form of eyeshadows, eyeliners or mascaras.

In the cosmetic compositions according to the invention, the fullerene or mixtures of fullerenes is/are generally present in a content of between 0.01 and 50% by weight relative to the total weight of the composition, this being dependent on the cosmetic effect sought.

The cosmetic make-up compositions according to the invention can, in addition, contain additional pigments and/or fillers which are common in cosmetics.

Among inorganic pigments, there may be mentioned as examples:

- titanium dioxide (rutile or anatase) where appropriate surface treated and codified in the Color Index under reference CI 77891;
- black, yellow, red and brown iron oxides, codified under references CI 77499, 77492, 77491;
- manganese violet (CI 77742);

ultramarine bluc (CI 77007);

hydrated chromium oxide (CI 77289);

ferric blue (CI 77510);

and all inorganic pigments which have undergone an inorganic or organic surface treatment.

Among organic pigments, special mention may be made of the following:

| | |
|---|---|
| D & C red No. 19 | (CI 45170); |
| D & C red No. 9 | (CI 15585); |
| D & C red No. 21 | (CI 45380); |
| D & C orange No. 4 | (CI 15510); |
| D & C orange No. 5 | (CI 45370); |
| D & C red No. 27 | (CI 45410); |
| D & C red No. 13 | (CI 15630); |
| D & C red No. 7 | (CI 15850-1); |
| D & C red No. 6 | (CI 15850-2); |
| D & C yellow No. 5 | (CI 19140); |
| D & C red No. 36 | (CI 12085); |
| D & C orange No. 10 | (CI 45425); |
| D & C yellow No. 6 | (CI 15985); |
| D & C red No. 30 | (CI 73360); |
| D & C red No. 3 | (CI 45430); |
| carbon black | (CI 77266); and |
| lakes based on cochineal carminc | (CI 75470). |

It is also possible to use nacreous pigments which may be chosen, in particular, from:

white nacreous pigments such as bismuth oxychloride and titanium oxide-coated mica; and coloured nacreous pigments such as titanium mica with iron oxides, titanium mica with ferric blue or chromium oxide, titanium mica with an organic pigment of the abovementioned type, as well as those based on bismuth oxychloride, and all organic pigments which have undergone an inorganic or organic surface treatment.

According to the invention, the additional pigments can represent from 0.01 to 90% by weight of the composition, preferably from 0.5 to 30%.

The fillers are chosen, in particular, from:

silica, talc, which is a hydrated magnesium silicate, used in the form of particles generally smaller than 40 μm in size; talc possesses moisture-absorbing properties and is used most particularly on account of its creamy feel;

micas, which are aluminosilicates of miscellaneous compositions, which take the form of scales from 2 to 200 μm, and preferably from 5 to 70 μm, in size, and from 0.1 to 5 μm, and preferably from 0.2 to 3 μm, in thickness. The micas may be of natural origin (for example muscovite, margarite, roscoelite, lepidolite, biotite) or of synthetic origin. The micas are generally transparent and enable the skin to be endowed with a satin-like appearance;

starch, especially rice starch;

kaolin, which is a hydrated aluminium silicate which takes the form of particles of isotropic form which are generally smaller than 30 μm in size and which possess good fat-absorption properties;

the zinc and titanium oxides, generally used in the form of particles not exceeding a few micrometers in size (or even smaller than 1 μm in the case of titanium oxide): these oxides have a creamy feel, good covering power and considerable opacity;

boron nitride;

precipitated calcium carbonate which, in the form of particles smaller than 10 μm in size, has a creamy feel and enables a matt appearance to be obtained;

magnesium carbonate or hydrogen carbonate, which possess, in particular, perfume-binding properties;

metal soaps derived from organic carboxylic acids having from 8 to 22 carbon atoms, and preferably from 12 to 18 carbon atoms, for example zinc, magnesium or lithium stearate, zinc laurate, magnesium myristate, and the like. These soaps, generally present in the form of particles smaller than 10 μm in size, have a creamy feel and facilitate adhesion of the powder to the skin;

powders of synthetic polymers such as polyethylene, polyesters (for example polyethylene isophthalate or terephthalate), polyamides, in the form of particles smaller than 50 μm in size, which possess absorbent properties and enable the skin to be endowed with a velvety appearance, methacrylate powders;

hollow microspheres such as, for example, the hollow microspheres of Expancel sold by the company KEMANORD PLAST AB and described in French Patent 86/09,289 (2,600,532).

According to the invention, the additional fillers can represent from 0.01 to 90% by weight of the composition.

The compositions according to the present invention can, in particular, take the form of an oil-in-water or water-in-oil emulsion, or the form of a suspension in a solvent medium, or alternatively the form of a free powder, compacted powder or anhydrous paste. The procedures for the preparation of these different types of compositions are well known to a person skilled in the art.

When they are used in emulsion form, the compositions can contain surfactants which are well known in the state of the art. These surfactants can constitute from 0.01 to 30% by weight of the composition.

An especially preferred embodiment consists in preparing anionic or nonionic emulsions using anionic or nonionic surfactants in proportions preferably of between 2 and 30% by weight relative to the total weight of the composition.

Among anionic surfactants which may be used alone or mixed, special mention may be made of the alkali metal salts, ammonium salts, amine salts or amino alcohol salts of the following compounds:

alkyl sulphates, alkyl ether sulphates, alkylamide sulphates and ether sulphates, alkylaryl polyether sulphates, monoglyceride sulphates, alkylsulphonates, alkylamide sulphonates, alkylarylsulphonates, α-olefine sulphonates, paraffin sulphonates, alkylsulphosuccinates, alkylether sulphosuccinates, alkylamide sulphosuccinates, alkylsulphosuccinamates, alkylsulphoacetates, alkylpolyglycerol carboxylates, alkyl phosphates/alkyl ether phosphates, acylsarcosinates, alkylpolypeptidates, alkylamidopolypeptidates, acylisethionates, alkyltaurates.

The alkyl or acyl radical of all these compounds generally denotes a chain of 12 to 18 carbon atoms.

Other anionic surfactants consist of salts of fatty acids such as oleic, ricinoleic, palmitic and stearic acids, the acids of coconut oil or of hydrogenated coconut oil and in particular, amine salts such as amine stearates.

There may also be mentioned:

acyllactylates in which the acyl radical comprises from 8 to 20 carbon atoms, polyglycol ether carboxylic acids corresponding to the formula:

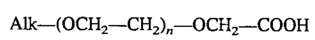

$$Alk—(OCH_2—CH_2)_n—OCH_2—COOH$$

in acid or salified form, where the substituent Alk, corresponds to a linear chain having from 12 to 18 carbon atoms and where n is an integer between 5 and 15.

Among nonionic surfactants which may be used alone or mixed, special mention may be made of: polyethoxylated, polypropoxylated or polyglycerolated alcohols, alkylphenols and fatty acids having a fatty chain containing 8 to 18 carbon atoms. There may also be mentioned copolymers of ethylene oxide and propylene oxide, condensates of propylene and ethylene oxide with fatty alcohols, polyethoxylated fatty amides, polyethoxylated fatty amines, ethanolamides, fatty acid esters of glycol, fatty acid esters of sorbitan, oxyethylenated or otherwise, fatty acid esters of sucrose, fatty acid esters of polyethylene glycol, phosphoric triesters and fatty acid esters of glucose derivatives.

Other compounds belonging to this class are the condensation products of an α-diol, monohydric alcohol, alkylphenol, amide or diglycolamide with glycidol or a precursor of glycidol.

The nonionic surfactants mainly used are polyethoxylated or polyglycerolated alcohols such as polyethoxylated stearyl, cetyl/stearyl or oleyl alcohols.

The anionic surfactants used preferentially are amine stearates.

The compositions according to the invention may also take the form of a gel or an aqueous or aqueous-alcoholic solution of one or more water-soluble polymers such as polyacrylic acid derivatives, or the form of emulsified gels obtained by dispersion of oils in gels using emulsifiers such as the "Pemulens" of the company GOODRICH.

The compositions according to the present invention can contain, in addition to the components mentioned above, ingredients traditionally used in cosmetic compositions, and chosen from demulcents, preservatives, sequestering agents, perfumes, thickeners, cohesion agents and polymers, as well as alkalinizing or acidifying agents customarily used in the cosmetic field, hydrating agents and water-soluble active substances.

The thickeners which are usable may be natural or synthetic. Among natural thickeners, gums of various kinds such as gum arabic, guar gum or carob gum may be mentioned. Among synthetic thickeners, cellulose derivatives such as hydroxyethylcellulose, carboxymethylcellulose, starch derivatives, cellulose ether derivatives possessing quaternary ammonium groups, cationic polysaccharides, salts of acrylic or methacrylic polymers, polyenes or polysiloxanes may be mentioned.

A thickening of the compositions may also be obtained by mixing polyethylene glycol and polyethylene glycol stearate and/or distearate, or with a mixture of phosphoric esters and fatty amides.

According to the invention, the oily phase may represent from 0.1 to 50% by weight of the emulsion.

It can consist of oils and/or waxes.

The waxes and oils can be of vegetable, animal, mineral or synthetic origin.

Among vegetable oils, jojoba oil, olive oil, sweet almond oil, avocado oil, coconut oil, wheatgerm oil, maize oil, palm oil, sesame oil, soya bean oil, argan oil, oenothera oil, borage oil and essential oils may be mentioned.

Among animal oils, fish oil may be mentioned in particular.

Among mineral oils, liquid paraffin and isohexadecane may be mentioned.

Among synthetic oils, ethyl and isopropyl palmitates, 2-ethylhexyl palmitate, alkylmyristates such as isopropyl, butyl and cetyl myristates, hexyl stearate, octanoic and decanoic acid triglycerides, cetyl ricinoleate and stearyl octanoate, silicone oils, perfluorinated oils and fluorinated silicone oils may be mentioned.

The oily phase can, moreover, contain colorants, sunscreen agents, antioxidants, preservatives and lipophilic active principles.

According to the invention, the anhydrous compositions, which may take the form of a free or compacted powder or solid, pasty or liquid cosmetic, can contain a binder which can preferably represent from 0.01 to 95% by weight.

Among binding agents, there may be mentioned, in particular, animal, vegetable or synthetic oils, mixtures of oil(s) and wax(es), and especially mink oil, turtle oil, soya bean oil, grape pip oil, sesame oil, maize oil, rapeseed oil, sunflower oil, cotton oil, avocado oil, olive oil, castor oil, jojoba oil, groundnut oil, and the like; hydrocarbon oils such as paraffin oils, squalene, petrolatum, and the like; esters such as isopropyl myristate, isopropyl palmitate, butyl stearate, hexyl laurate, isononyl isononanate, 2-ethylhexyl palmitate, 2-hexyldecyl laurate, 2-octyldecyl palmitate, 2-octyldodecyl myristate, di(2-ethylhexyl) succinate, diisostearyl malate, 2-octyldodecyl lactate, glyceryl triisostearate, diglyceryl triisostearate and the like; silicone oils such as poly(methylsiloxanes), poly(methylphenylsiloxanes), polysiloxanes modified by fatty acids, polysiloxanes modified by fatty alcohols, polysiloxanes modified by polyoxyalkylenes, fluorinated silicones, and the like; perfluorinated and/or organofluorinated oils; higher fatty acids such as myristic acid, palmitic acid, stearic acid, behenic acid, oleic acid, linoleic acid, linolenic acid, isostearic acid, and the like; higher fatty alcohols such as cetanol, stearyl alcohol, oleyl alcohol, and the like; the waxes may be chosen, in particular, from carnauba wax, candelilla wax, beeswax, spermaceti, lanolins, microcrystalline waxes, and the like.

The binder can contain, in addition, volatile oils which will evaporate in contact with the skin, but whose presence in the cosmetic composition is useful since they facilitate spreading of the composition on application to the skin. Such spreading agents, referred to here as "volatile oils", are generally oils having a saturated vapour pressure at 25° C. equal to at least 0.5 millibar (equivalent to $0.5 \times 10^2$ Pa).

Among volatile oils which may be present as spreading agents in the composition of the invention, there may be mentioned, for example, silicone oils such as hexamethyldisiloxane, cyclopentadimethylsiloxane, cyclotetramethylsiloxane, fluorinated oils such as that marketed under the name GALDEN (MONTEFLUOS) or isoparaffinic oils such as those marketed under the name ISOPAR (E, G, L or H).

As mentioned above, the compositions according to the invention can also take the form of a nail varnish in an aqueous medium containing from 0.01 to 10% by weight of fullerene or of a mixture of fullerenes.

The nail varnishes comprise a synthetic film-forming aqueous dispersion containing a water-miscible or -dispersible substance, to which may be added a film-forming material and common additives such as a thickener, a pH regulator, a crosslinking agent, an antifoam, and the like.

Dispersions of polyvinyl acetate, polyurethane, acrylic polymers or copolymers and polyvinyl acetate copolymers may be used, inter alia, as a synthetic aqueous dispersion.

According to the invention, the synthetic aqueous dispersion represents approximately from 10 to 80% by weight of the varnish.

The film-forming material is generally present at a concentration of between 5 and 20% by weight relative to the total weight of the varnish.

Among film-forming materials, water-soluble cellulose derivatives may be mentioned in particular.

The varnishes according to the invention can also contain a resin, generally present at a concentration of between 0.5 and 15% by weight relative to the total weight of the varnish.

Among resins which are usable, resins of the acrylic, styrene, acrylate/styrene and vinyl type may be mentioned in particular.

The nail varnishes according to the invention can also contain adjuvants commonly used in nail varnishes, such as, for example, UV screening agents.

Several examples of cosmetic make-up compositions according to the invention will now be given by way of illustration.

EXAMPLE 1: Mascara in Emulsion Form

| | |
|---|---|
| Triethanolamine stearate | 15.0 g |
| Beeswax | 8.0 g |
| Paraffin | 3.0 g |
| Colophony | 2.0 g |
| Ozocerite | 10.0 g |
| Propyl para-hydroxybenzoate | 2.0 g |
| Methyl para-hydroxybenzoate | 2.0 g |
| Gum arabic | 0.5 g |
| Hydroxyethylcellulose | 1.0 g |
| $C_{60}/C_{70}$ fullerene (Fullerite sold by the company ALDRICH) | 5.0 g |
| Water qs | 100.0 g |

When applied to the eyelashes, this mascara imparts a dark brown make-up.

EXAMPLE 2: Eyeliner in Suspension Form

| | |
|---|---|
| Vinylpyrrolidone/vinyl acetate copolymer | 12.5 g |
| Polyvinyl alcohol | 0.5 g |
| Oleyl alcohol condensed with 15 mol of ethylene oxide | 2.5 g |
| Propylene glycol | 7.5 g |
| Ethyl alcohol | 3.0 g |
| Polyacrylate - sodium salt | 0.5 g |
| Methyl para-hydroxybenzoate | 0.3 g |
| $C_{60}/C_{70}/C_{84}$ fullerene (sold by TEXAS FULLERENE CORP.) | 6.0 g |
| Water qs | 100.0 g |

The make-up imparted by the eyeliner is dark brown.

EXAMPLE 3: Conventional Style Lipstick

| | |
|---|---|
| Butylated hydroxytoluene | 0.15 g |
| Lanolin | 17.50 g |
| Microcrystalline wax | 15.00 g |
| Caprylic/capric triglycerides | 11.00 g |
| Octylglyceryl behenate | 11.00 g |
| Titanium mica | 6.00 g |
| $C_{60}/C_{70}$ fullerene (Fullerite sold by the company ALDRICH) | 0.30 g |
| Iron oxides | 2.70 g |
| Castor oil qs | 100.0 g |

The colour of the lipstick is red-brown.

EXAMPLE 4: Compact Face Powder

| | |
|---|---|
| Polyethylene powder | 5.00 g |
| Mica | 12.00 g |
| Isopropyl myristate | 1.50 g |
| Liquid paraffin | 1.50 g |
| Yellow iron oxide | 0.80 g |
| Orange iron oxide | 0.60 g |
| $C_{60}/C_{70}/C_{84}$ fullerene (sold by TEXAS FULLERENES CORP.) | 0.15 g |
| Talc qs | 100.0 g |

The compact powder is brown in colour.

EXAMPLE 5: Tinted Gel-Cream

| | |
|---|---|
| Acrylic acid/$C_{10}/C_{30}$ alkyl acrylate copolymer (sold under the name "PERMULEN-TR-1" by the company GOODRICH) | 0.10 g |
| CARBOPOL 940 of the company GOODRICH | 0.60 g |
| Triethanolamine | 0.80 g |
| Glycerol | 3.00 g |
| Preservative | 0.20 g |
| Cyclomethicone | 25.00 g |
| Nylon 12 | 5.00 g |
| Iron oxide | 0.75 g |
| $C_{60}/C_{70}/C_{84}$ fullerene (sold by TEXAS FULLERENES CORP.) | 0.10 g |
| Titanium oxide | 4.15 g |
| Water qs | 100.0 g |

The gel obtained is brown in colour.

EXAMPLE 6: Make-Up Foundation

| | |
|---|---|
| Glyceryl stearate | 2.20 g |
| Caprylic/capric acid triglycerides | 15.00 g |
| Methyl para-hydroxybenzoate | 0.10 g |
| Propyl para-hydroxybenzoate | 0.10 g |
| Imidazolidinylurea | 0.30 g |
| 2-Hydroxy-4-methoxybenzophenone | 0.50 g |
| 2-Ethylhexyl dimethyl-p-aminobenzoate (sold under the name "ESCALOL 507" by the company VAN DYK) | 0.50 g |
| Aluminium magnesium silicate | 1.00 g |
| Triethanolamine | 1.00 g |
| Carboxymethylcellulose | 0.16 g |
| Aluminium starch octenylsuccinate (sold by the company NATIONAL STARCH under the name "DRY FLO" | 5.00 g |
| Cyclomethicone | 10.00 g |
| Propylene glycol | 2.00 g |
| Glycerol | 3.00 g |
| Sodium lauroyloarcosinate | 0.60 g |
| Stearic acid | 2.20 g |
| Yellow iron oxide | 2.00 g |
| Red iron oxide | 1.40 g |
| $C_{60}/C_{70}$ fullerene (Fullerite sold by the company ALDRICH) | 0.60 g |
| Titanium oxide | 8.00 g |
| Water qs | 100 g |

The make-up foundation is brown in colour.

I claim:

1. A cosmetic composition in the form of an oil-in-water or water-in-oil emulsion containing an effective amount of fullerene or mixture of fullerenes as a pigment or filler, and a surfactant in a proportion of between 0.01 and 30% by weight, the oily phase of the emulsion being between 0.1 and 50% by weight relative to the total weight of the composition.

2. An anhydrous cosmetic composition selected from the group consisting of free powder, compacted powder, solid, pasty and liquid cosmetic containing, in a suitable cosmetic vehicle, an effective amount of a fullerene or mixture of fullerenes as a pigment or filler, and a binding agent present in a proportion between 0.01 and 95% by weight relative to the total weight of the composition.

3. A cosmetic composition in the form of an aqueous nail varnish, comprising, as a pigment or filler, an effective amount of a fullerene or mixture of fullerenes, said varnish containing:

from 10 to 80% by weight of an aqueous synthetic dispersion of a polymer selected from the group consisting of polyvinyl acetate, polyurethane, acrylic polymers, acrylic copolymers and polyvinyl acetate copolymers, from 5 to 20% by weight of a film-forming material, and from 0.5 to 15% by weight of a resin.

4. Composition according to claim 3, which contains from 0.01 to 10% by weight of fullerene or of a mixture of fullerenes.

5. A cosmetic make-up composition comprising, in a suitable cosmetic vehicle for said make-up composition, an effective amount of a fullerene or mixture of fullerenes as a pigment or filler, and at least one cosmetic ingredient selected from the group consisting of demulcents, preservatives, sequestering agents, perfumes, and cohesion agents.

6. Cosmetic composition according to claim 5, wherein the fullerene is selected from the group consisting of $C_{60}$, $C_{70}$, $C_{84}$ carbon atoms and mixtures thereof.

7. Cosmetic composition according to claim 5, wherein the fullerene is $C_{60}$ carbon atoms.

8. Cosmetic composition according to claim 5 wherein the mixture of fullerenes is $C_{60}/C_{70}$ carbon atoms.

9. Cosmetic composition according to claim 5 which contains the fullerene or mixture of fullerenes in a proportion of between 0.01 and 50% by weight relative to the total weight of the composition.

10. Cosmetic composition according to claim 5 which further contains an additional pigment at a concentration of between 0.01 and 90% by weight relative to the total weight of the composition.

11. Cosmetic composition according to claim 5 which further contains an additional filler present at a concentration of between 0.01 and 90% by weight relative to the total weight of the composition.

12. A cosmetic composition according to claim 5, wherein said cosmetic composition is selected from the group consisting of eyeshadow, eyeliner, mascara, powder, make up foundation, rouge, blusher, tinted cream, lipstick and nail varnish.

13. A method of cosmetic treatment, comprising applying a composition containing a vehicle and a fullerene or mixture of fullerenes.

14. The method of claim 13, wherein the fullerene is selected from the group consisting of $C_{60}$, $C_{70}$, $C_{84}$ carbon atoms and mixtures thereof.

15. The method of claim 13, wherein the fullerene has $C_{60}$ carbon atoms.

16. The method of claim 13, wherein the mixture of fullerenes has $C_{60}/C_{70}$ carbon atoms.

17. The method of claim 13, wherein the fullerene or mixture of fullerenes is in a proportion of between 0.01 and 50% by weight relative to the total weight of the composition.

18. The method of claim 13, wherein said composition further contains an additional pigment at a concentration of between 0.01 and 90% by weight relative to the total weight of the composition.

19. The method of claim 13, wherein the composition further contains a filler present at a concentration of between 0.01 and 90% by weight relative to the total weight of the composition.

20. The method of claim 13, wherein the composition is in the form of an oil-in-water emulsion, water-in-oil emulsion, suspension, free powder, compacted powder, solid, anhydrous paste or aqueous nail varnish.

21. The method of claim 20, wherein the composition is in the form of an oil-in-water or water-in-oil emulsion containing a surfactant in a proportion of between 0.01 and 30% by weight, the oily phase of the emulsion being between 0.1 and 50% by weight relative to the total weight of the composition.

22. The method of claim 20, wherein the composition is in the form of a solid or anhydrous paste and contains at least one binding agent present in a proportion of between 0.01 and 95% by weight relative to the total weight of the composition.

23. The method of claim 13, wherein the composition is in the form of an aqueous nail varnish containing:

from 10 to 80% by weight of a synthetic dispersion;

from 5 to 20 weight percent of a film-forming material; and from 0.5 to 15% by weight of a resin.

24. The method of claim 13, wherein the composition contains from 0.01 to 10% by weight of fullerene or mixture of fullerenes.

25. The method of claim 13, comprising applying said composition to the skin, eyes, nail or hair.

* * * * *